(12) United States Patent
Papadopoulos

(10) Patent No.: US 7,785,102 B2
(45) Date of Patent: Aug. 31, 2010

(54) ORTHODONTIC DEVICE

(76) Inventor: Moschos A. Papadopoulos, Dion. Solomou Str. 12, Serres, GR-62122 (GR)

( * ) Notice: Subject to any disclaimer, the term of this patent is extended or adjusted under 35 U.S.C. 154(b) by 409 days.

(21) Appl. No.: 11/822,779

(22) Filed: Jul. 10, 2007

(65) Prior Publication Data

US 2008/0020339 A1    Jan. 24, 2008

(30) Foreign Application Priority Data

Jul. 21, 2006 (DE) .................. 10 2006 033 774

(51) Int. Cl.
*A61C 3/00* (2006.01)
(52) U.S. Cl. .......................... 433/21; 433/18
(58) Field of Classification Search .............. 433/18, 433/19, 20, 21, 24
See application file for complete search history.

(56) References Cited

U.S. PATENT DOCUMENTS 4,272,240 A    6/1981 Glassman
6,719,557 B1 *  4/2004 Williams ................ 433/19
6,908,306 B2    6/2005 Bowman et al.

FOREIGN PATENT DOCUMENTS

DE    43 34 487 C1    12/1994
DE    299 23 123 U1    5/2000

* cited by examiner

*Primary Examiner*—Cris L Rodriguez
*Assistant Examiner*—Eric Rosen
(74) *Attorney, Agent, or Firm*—Manabu Kanesaka

(57) ABSTRACT

An orthodontic device for shifting a molar tooth along the maxillary arch includes an elongated guide element, on whose one end a first securing element is installed to secure the guide element relative to the maxillary arch. A first tube is formed to be shiftable on the guide element, wherein the first tube has a first securing device for optionally securing the first tube relative to the guide element. A second tube is guided on the first tube like a telescope arm, wherein the second tube has a second securing element for securing to the molar tooth. A spring is disposed to act between the first and the second tube which forces the second tube in a direction away from the first securing device.

10 Claims, 7 Drawing Sheets

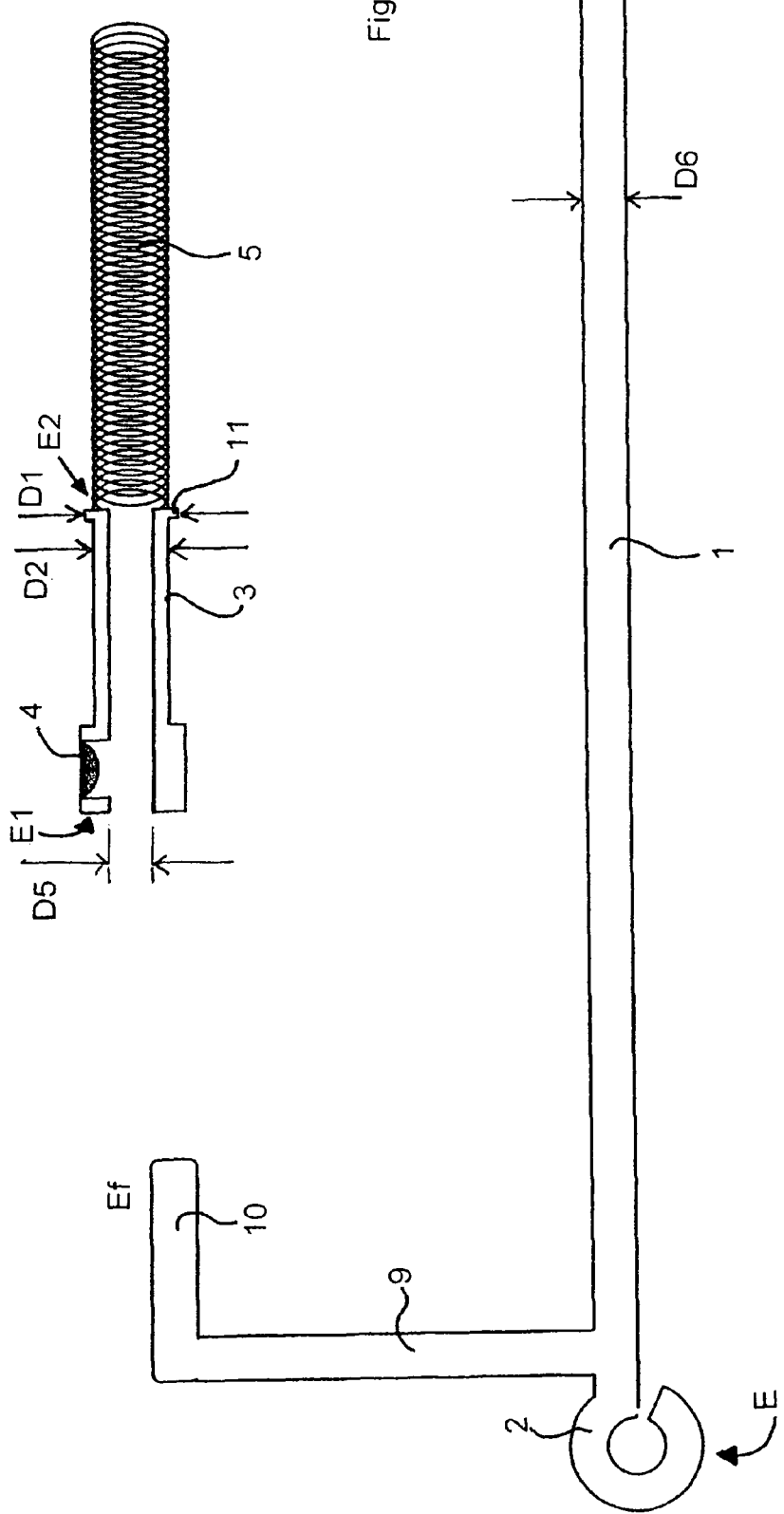

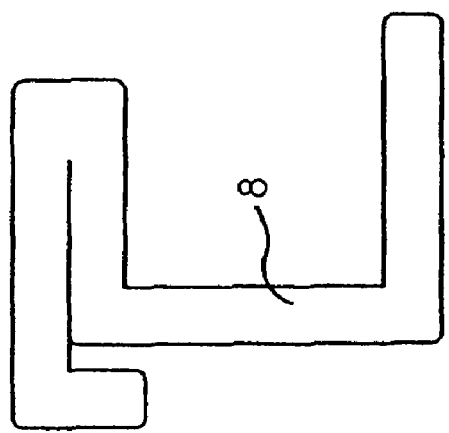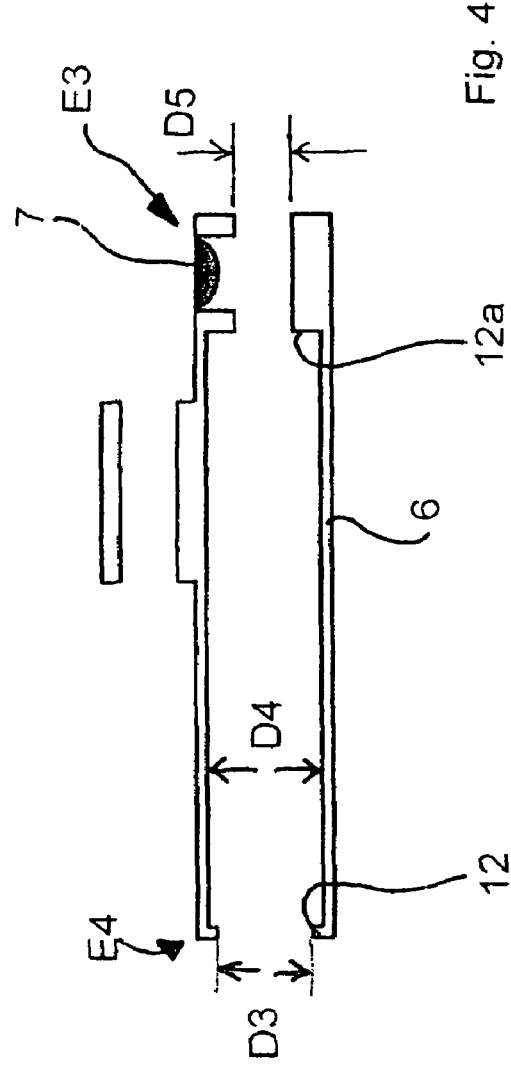

ORTHODONTIC DEVICE

FIELD OF THE INVENTION

The invention relates to an orthodontistic device for shifting a molar along the maxillary arch.

BACKGROUND OF THE INVENTION

U.S. Pat. No. 6,908,306 B2 discloses an orthodontic device for the distal shifting of a molar along the maxillary arch. The known device consists of an elongated guide element on whose one end a securing mechanism is installed to secure the guide element relative to the alveolar crest. A shiftable stop is fixated by clamping on the guide element. A further stop is held shiftably to the guide element and simultaneously connected to the molar to be shifted. Between the fixed stop and the shiftable stop is a spring which forces the shiftable stop and thus also the molar connected thereto in a distal direction.

The known device has a plurality of edges and protrusions which the patient experiences as uncomfortable and which are also detrimental to oral hygiene. Apart from this, the installation of the known device requires some skill. After all, the device disadvantageously not only causes the desired distal movement of the molar but also an undesired rotation of same. If the device is supported on the front teeth, an undesired mesial movement of the front teeth may occur.

SUMMARY OF THE INVENTION

The object of the invention is to eliminate the disadvantages as per the state of technology. In particular, an easy-to-install orthodontistic device is to be specified which is better accepted by the patient. As a further goal of the invention, the orthodontistic device is also to particularly prevent undesired tipping and/or rotating movements of the molar.

According to the invention, an orthodontic device for the shifting of a molar tooth along the maxillary arch is provided with an elongated guide element on whose one end a first securing element is installed to secure the guide element relative to the maxillary arch, a first tube being shiftable on the guide element, the first tube having a first securing device for optional securing the first tube relative to the guide element, a second tube being guided on to the first tube like a telescope arm, the second tube having a second securing element for securing to the molar tooth and a spring acting between the first and the second tube which forces the second tube in a direction away from the first securing device.

As provided by the invention by using a first tube and a second tube being guided on the first tube as well as the guide element with a spring in between the two, an encapsulated construction is created which has fewer corners and edges as the devices known from the prior art. The suggested device, which is provided to be secured at the palatinal side the molar tooth, is better accepted by the patient. Apart from this, the interaction of the first and the second tube as well as the guide element creates a particularly rigid structure which permits a precise, straight distal movement of the molar. The suggested construction counteracts in particular an undesired rotating movement of the molar. Finally the suggested device is particularly easy to install. It can be attached in a single piece and activated by securing the first tube via the first securing device.

As per an advantageous embodiment, the first securing device is provided on a first end of the first tube and the spring is supported on the second end located opposite. To increase ease of installation, the spring can also be mounted on the second end. A second securing device for the optional securing of the second tube relative to the guide element can also be provided on the second tube. The second securing device is usefully provided on a third end of the second tube. With the first and/or second securing device, this is usefully one or more clamping unit/units. The first and/or second tube can be fixated relative to the guide element with a clamping screw in a particularly advantageous embodiment. This enables particularly simple securing of the first and/or second tube relative to the guide element.

In a further embodiment, the first tube has a first protrusion protruding to the outside on its second end and the second tube has a second protrusion protruding radially to the inside on the fourth end opposite the third end, wherein the first and the second protrusion act together as a stop for limitation of the movement of the second tube caused by the spring. In accordance with the suggested embodiment, the second tube is held on the first tube so that it is shiftable but cannot be lost. The interaction of the first and the second protrusion simultaneously limits a maximum movement of the telescopic-like guided second tube.

In a particularly advantageous embodiment of the invention, the first protrusion is a radially circumferential protrusion with a first outer diameter and the second protrusion is a radially circumferential protrusion with a first inner diameter, wherein a second outer diameter of the first tube approximately corresponds to the first inner diameter of the second protrusion and the first outer diameter of the first protrusion approximately corresponds to a second inner diameter of the second tube, so that the second tube is shiftably conducted with its fourth end on the first tube. Naturally, when implementing the shiftable guide, the second outer diameter of the first tube is slightly smaller than the first inner diameter of the second protrusion and the first outer diameter of the first protrusion is slightly smaller than the second inner diameter of the second tube. The interaction of the protrusions can limit a maximum movement of the second tube relative to the first tube, on the one hand, and, on the other hand, can also implement a particularly exact straight guide of the second tube relative to the first tube. Up to when a maximum extended end position of the second tube is reached, the second tube is always supported on the first tube by the first and second protrusions. This counteracts an undesired tipping movement of the second tube.

In a further embodiment of the invention, it is provided that the second tube is shiftably guided with its third end on the guide element. The suggested additional guidance of the second tube on the guide element can achieve further improved guidance and thus an even better straightness of the movement.

A holding device is usefully attached on the guide element in the vicinity of the securing element. The holding element is secured at a maximum distance of 10 mm from the securing element on the guide element. Securing can be implemented via soldering, for example.

The securing element is usefully an eye through which an implant anchored in the jaw bone, in particular in the palatine bone, is passed. This provides safe and reliable securing of the orthodontistic device. As an alternative, the securing element can also be a plate anchored on several teeth and supported against the palate.

The holding device is usefully a wire extending essentially vertically from the guide element, the free end of which wire is bent at an angle of 70 to 110°. The wire lies on the occlusal surface of a further tooth located between the molar and the incisors and counteracts an undesired rotation of the guide element. The guide element is thus fixated on two points so that the desired longitudinal movement of the molar to be shifted can be safely and reliably implemented.

BRIEF DESCRIPTION OF THE DRAWINGS

An example will now be used to describe the embodiments of the invention in more detail based on the drawings. The figures are listed below:

FIG. 2 a schematic sectional view of the guide element as per FIG. 1,

FIG. 3 a schematic sectional view of the first tube with spring as per FIG. 1,

FIG. 4 a schematic sectional view of the second tube as per FIG. 1,

FIG. 5 a schematic sectional view of the second securing mechanism as per FIG. 1, FIG. 6 a top view of an upper jaw with device installed therein as per FIG. 1, FIG. 7 a top view of an upper jaw with devices installed therein as per FIG. 1, FIG. 8 a top view of an upper jaw with a second device as provided by the invention installed therein and FIG. 9 a top view of an upper jaw with a third device as provided by the invention installed therein.

DETAILED DESCRIPTION OF THE DRAWINGS

Figure 1:
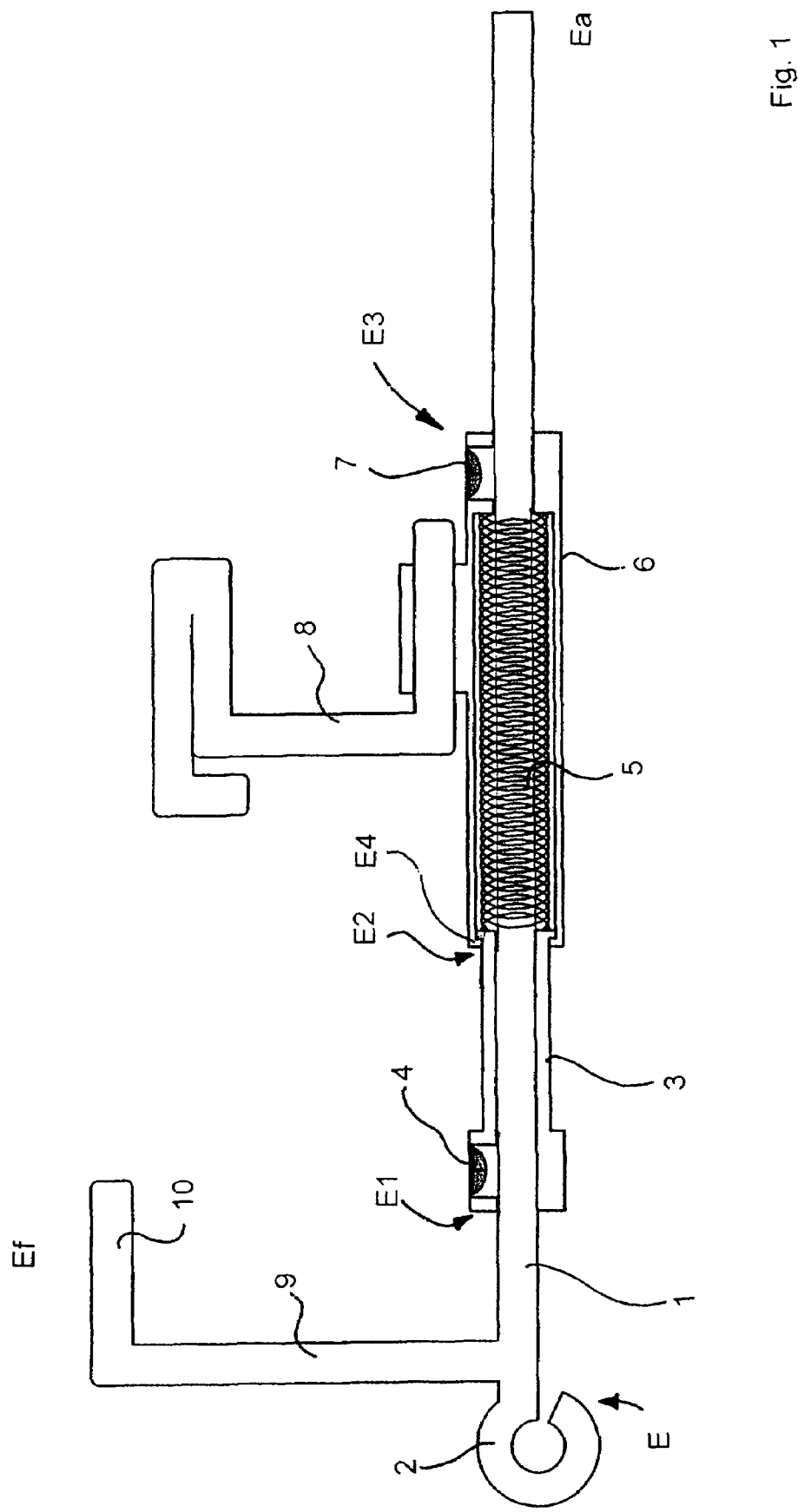
FIG. 1 a schematic sectional view of a first device provided by the invention.

FIG. 1 shows a schematic sectional view of a first device as provided by the invention. An elongated guide element 1 is made from a wire, preferably made of stainless steel, made with a thickness of 0.7 to 1.2 mm, preferably 0.9 mm. On one end E the guide element has a first securing element 2 formed as an eye which permits a further securing element, for example a screw implant, to be passed through. On the guide element 1 is a first tube 3 installed so that it can be shifted. The first tube 3 has a first securing device 4 on a first end E1. This is a clamping screw in a thread with which screw the first tube 3 can be fixated relative to the guide element 1. A spiral spring 5 is supported on a second end E2 of the first tube, which spring surrounds the guide element 1. The first tube 3 has a telescope-arm-like second tube 6. A second securing device 7 is provided on a third end E3 of the second tube 6. This in turn is a clamping screw in a thread with which screw the second tube 6 can be fixated by clamping relative to the guide element 1. Furthermore, on the second tube 6 is provided a second securing element 8 with which the second tube 6 can be fixated to a band encircling the tooth to be shifted. The second securing element 8 can be made of stainless steel wire which has a diameter in the range of 0.7 to 1.2 mm, preferably 0.9 mm.

In the vicinity of the first securing element 2, a holding element 9 extends away in an essentially vertical direction, which mechanism has in the area of its free end Ef a curvature 10 by an angle of 70 to 100°, preferably from 80 to 100°.

FIG. 2 to FIG. 5 again show schematic sectional views of the essential components of the device as per FIG. 1. As is particularly shown in FIG. 3, the second end E2 of the first tube 1 has a radially protruding to the outside, circumferential first protrusion 11 with a first outer diameter D1. The first tube 3 has a second outer diameter D2 which is smaller in comparison to the first diameter D1.

With reference to FIG. 4, the second tube 6 on a fourth end E4 opposite the third end E3 has a radial second circumferential protrusion 12 pointing inward whose first inner diameter is marked with the reference sign D3. A second inner diameter of the tube 6 is marked with the reference sign D4. The second inner diameter D4 is greater than the first inner diameter D3. The second outer diameter D2 of the first tube 3 and the first inner diameter D3 of the second protrusion 12 of the second tube 6 is selected so that the second tube 6 can be shifted on the first tube 3. Furthermore, the first outer diameter D1 of the first protrusion 11 and the third inner diameter D3 of the second protrusion 12 are selected so that the second tube 6 is held to the first tube 3 and cannot be lost. This means that, with a maximum extension of the second tube 6 relative to the first tube 3, the first 11 and the second protrusion 12 abut against each other and hinder further movement of the second tube 6 relative to the first tube 3. Furthermore, as is shown in FIG. 3, the spiral spring 5 can be fixated on the second end E2 of the first tube 3.

A fifth inner diameter D5 of the first tube 3 is selected somewhat larger than a sixth outer-diameter D6 of the guide element 1 so that the first tube 3 can be shifted on the guide element 1. Likewise, the second tube 6 also has the fifth inner diameter D5 in the area of the second securing device 7. The third protrusion 12a radially protruding inward and created by the fifth inner diameter D5 in the second tube 6 on the third end E3 is used to support the spiral spring 5.

Finally, it must be noted that a further eye or other suitable mechanism for the limitation of a movement of the tubes 3, 6 which can be shifted on the guide element 1 can be provided in the area of another end Ea of the guide element 1 located opposite the one end E.

Figure 6:
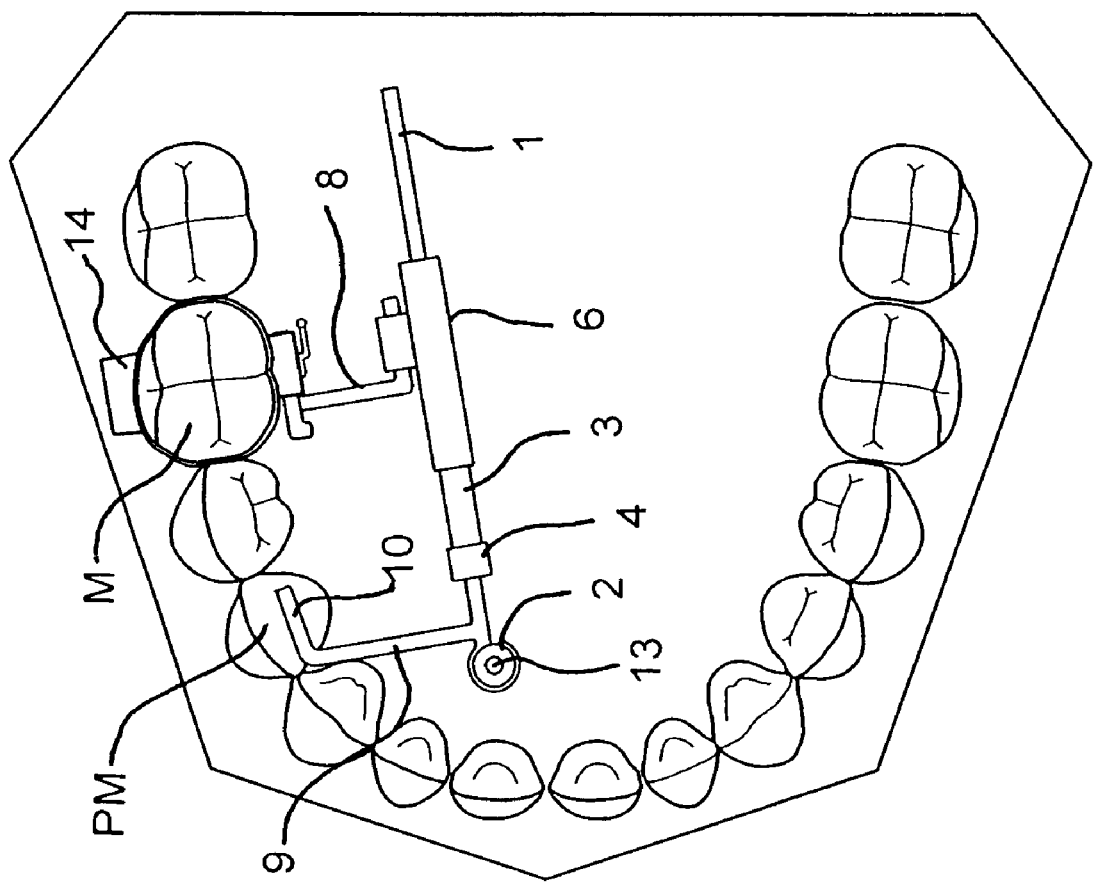

FIG. 6 shows a top view of a device installed in the upper jaw as per FIG. 1. The first securing element 2 is penetrated by a screw implant 13 which is screwed into the jaw bone. This securely and reliably holds the guide element 1 relative to the jaw bone. The bend 10 of the holding mechanism 9 is placed on the occlusal surface of a premolar tooth PM and additionally fixates the guide element 1. The second securing element 8 is fixated on a band 14 which surrounds the molar tooth M that is to be shifted.

Figure 7:
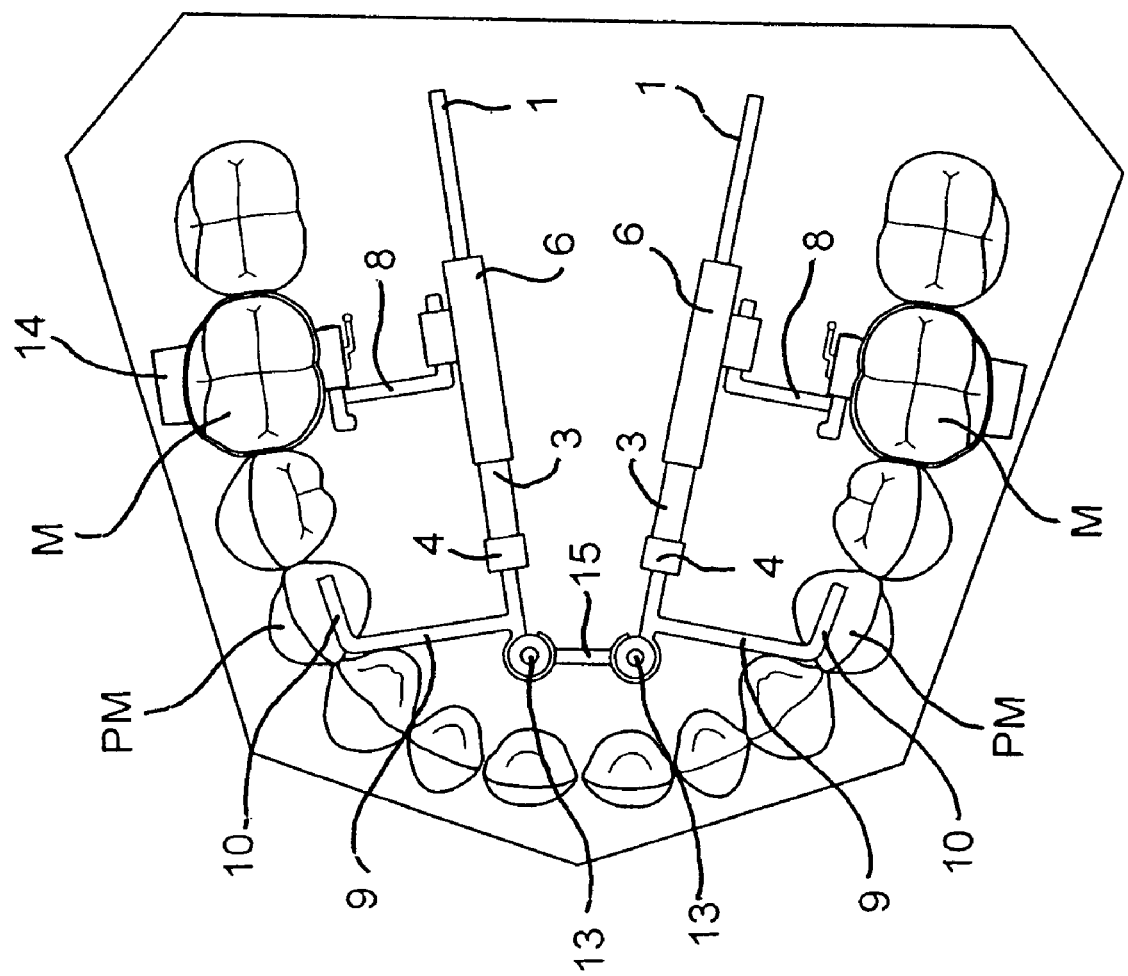

In the additional top view shown in FIG. 7 are two devices as per FIG. 1 each fixated via a screw implant 13 in the jaw bone. The two screw implants 13 can also be connected with each other with a connection ridge 15. Two molar teeth M opposite each other can be simultaneously shifted in a distal direction with the device shown in FIG. 7.

Figure 8:
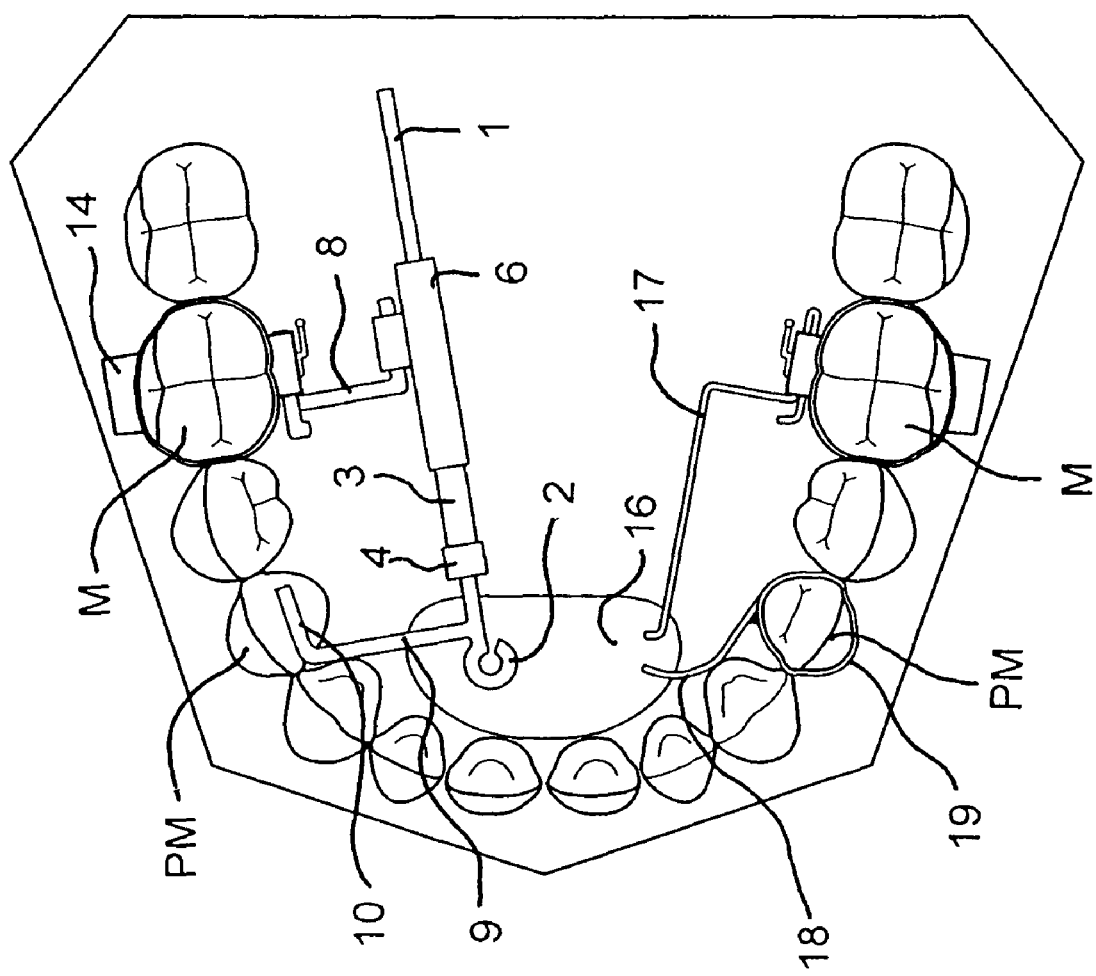

FIG. 8 shows a further top view of a second device. The first securing element 2 is mounted on a bolt extending from a plate 6 placed on the palate. The plate 16 is permanently connected with a third securing mechanism 17, which can be a wire extending from the plate 16, with a band 14 surrounding a molar tooth M. Furthermore, the plate 16 is permanently connected with a fourth securing element 18, which can in turn be a wire, with a further band 19 which surrounds a premolar tooth PM. The device as per FIG. 1 is installed on the opposite side of the jaw as previously described. To this extent, reference is made to the previous descriptions.

Figure 9:
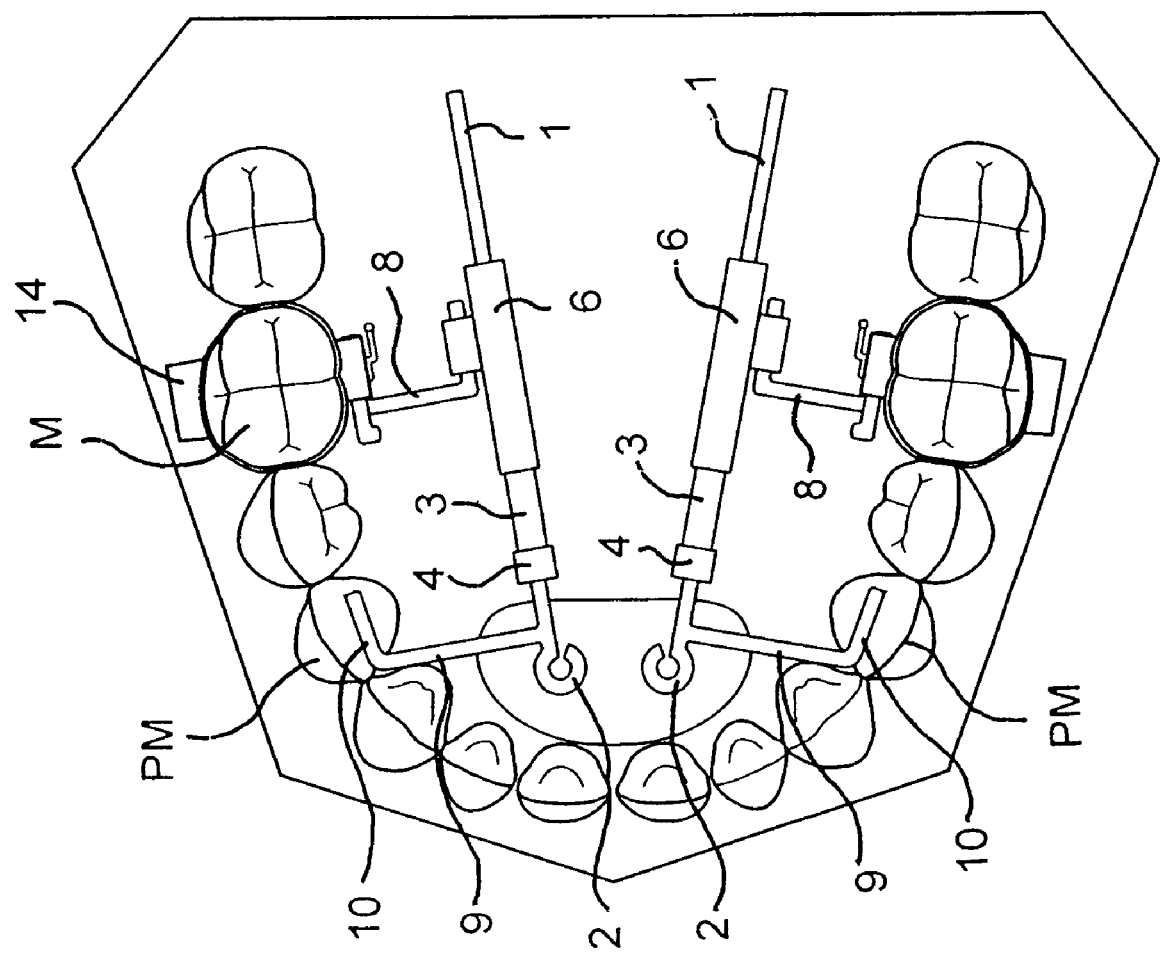

FIG. 9 shows a top view of a third device. Two devices as provided by the invention as per FIG. 1 are fixated with their first securing element 2 to the plate 16. Each of the devices is fixated via one second securing element 8 each to the band 14 surrounding the molar tooth M. Furthermore, each of the devices is also fixated with the holding element 9 to a premolar tooth PM.

The function of the shown devices is the following:

With the cases shown in FIG. 6 to 9, the first tube 3 is fixated with the first securing device 4 to the guide element 1 and cannot be shifted. The fixation of the first tube 3 on the guide element 1 is such that the spiral spring is pressed together. The second tube 6 which is held shiftably on the first tube 3 is forced by the spiral spring 5 supported against the first 11 and the third protrusion 12a in a distal direction. The second tube 6 is connected via the second securing element 8 with the molar tooth M to be shifted. The force vector generated by the spring exerts pressure on the molar tooth M in the vicinity of the center of the greatest resistance. This permits a linear movement along the alveolar crest without an undesired turning or tilting of the molar tooth M. The spiral spring 5 exerts an essentially constant force on the molar tooth M which is sufficiently great to cause a distal movement of same. The force vector is also parallel to the occlusal level of the teeth. The fixation of the device via screw implants enables a particularly safe and reliable anchor.

After a distal shift of the molar tooth M by a specified distance, the device provided by the invention can be put into a passive state. The second tube 6 is fixated with the provided second securing device 7 relative to the guide element 1. No further movement of the shifted molar tooth M is possible in this state. The molar tooth M is securely anchored there with the device provided by the invention. In this state it itself can serve as an anchor to secure elastic elements for the movement of the premolar teeth PM, the eyeteeth and the incisor teeth in the distal direction.

REFERENCE DESIGNATION LIST

1 Guide element
2 First securing element
3 First tube
4 First securing device
5 Spiral spring
6 Second tube
7 Second securing device
8 Second securing element
9 Holding device
10 Bend
11 First protrusion
12 Second protrusion
12a Third protrusion
13 Screw implant
14 Band
15 Connection ridge
16 Plate
17 Third securing element
18 Fourth securing element
19 Additional band
D1 First outer diameter
D2 Second outer diameter
D3 First inner diameter
D4 Second inner diameter
D5 Fifth inner diameter
D6 Sixth outer diameter
E End
Ea Other end
Ef Free end
E1 First end
E2 Second end
E3 Third end
E4 Fourth end
M Molar tooth
PM Premolar tooth

The invention claimed is:

1. Orthodontic device for shifting of a molar tooth along a maxillary arch, comprising:

an elongated guide element having a first end and a first securing element disposed thereon to secure the guide element relative to the maxillary arch, a first tube having a first end and a second end, the first tube being adjustably fixed on the guide element that passes therethrough, so that the first end of the first tube is nearest the first end of the elongated guide element, the first tube having a first securing device disposed on the first end for securing the first tube relative to the guide element, a telescoping second tube having a first end and a second end, the second tube held shiftably on the first tube, the second tube having a second securing element disposed thereon for securing to the molar tooth and a spring surrounding the guide element and fully contained within the second tube, the spring being biased between the second end of the first tube and the second end of the second tube, the spring forcing the second tube and the second securing element disposed thereon, in a direction away from the first securing device;

wherein the elongated guide element extends completely through the first and second tubes.

2. Orthodontic device as defined in claim 1, wherein a second securing device is provided on a third end of the second tube for securing of the second tube relative to the guide element and placing the orthodontic device in a passive state.

3. The orthodontic device as defined in claim 2, wherein the first securing device and/or second securing device is/are a clamping unit/units.

4. The orthodontic device as defined in claim 2, wherein the first tube has a first protrusion protruding to the outside on a second end and the second tube has a second protrusion protruding radially to the inside on a fourth end opposite the third end, wherein the first and the second protrusions act together as a stop for limitation of the movement of the second tube caused by the spring.

5. Orthodontic device as defined in claim 4, wherein the first protrusion is a radially circumferential protrusion with a first outer diameter and the second protrusion is a radially circumferential protrusion with a first inner diameter, wherein a second outer diameter of the first tube approximately corresponds to the first inner diameter of the second protrusion and the first outer diameter of the first protrusion approximately corresponds to a second inner diameter of the second tube, so that the second tube is shiftably guided with the fourth end on the first tube.

6. The orthodontic device as defined in claim 2, wherein the second tube is shiftably guided with the third end on the guide element.

7. The orthodontic device as defined in claim 1, wherein a holding device having a free end is installed on the guide element in the vicinity of the first securing element.

8. The orthodontic device as defined in claim 1, wherein the first securing element is an eye through which an implant for anchoring a jaw is adapted to pass.

9. The orthodontic device as defined in claim 1, wherein the first securing element comprises a plate capable of being supported against a palate and anchored to several teeth.

10. The orthodontic device as defined in claim 9, wherein the holding device is a wire extending essentially vertically from the guide element, wherein said wire is bent on its free end around by an angle of 70 to 100 degrees.

* * * * *